United States Patent
Hsu et al.

(10) Patent No.: US 10,935,525 B2
(45) Date of Patent: Mar. 2, 2021

(54) METHOD FOR DETECTING A GAS SAMPLE USING A CARBON AEROGEL ADSORBENT

(71) Applicant: Kun Shan University, Tainan (TW)

(72) Inventors: Hao-Lin Hsu, Tainan (TW); Chung-Yih Kuo, Tainan (TW); Jean-Hong Chen, Tainan (TW)

(73) Assignee: KUN SHAN UNIVERSITY, Tainan (TW)

( * ) Notice: Subject to any disclaimer, the term of this patent is extended or adjusted under 35 U.S.C. 154(b) by 210 days.

(21) Appl. No.: 16/207,125

(22) Filed: Dec. 1, 2018

(65) Prior Publication Data

US 2020/0173969 A1    Jun. 4, 2020

(51) Int. Cl.
*G01N 30/00* (2006.01)
*B01J 20/281* (2006.01)
*G01N 30/54* (2006.01)
*G01N 30/72* (2006.01)
G01N 30/02 (2006.01)
G01N 30/52 (2006.01)

(52) U.S. Cl.
CPC ............ *G01N 30/48* (2013.01); *G01N 30/54* (2013.01); *G01N 30/7206* (2013.01); *G01N 2030/025* (2013.01); *G01N 2030/486* (2013.01); *G01N 2030/521* (2013.01)

(58) Field of Classification Search
CPC .... G01N 30/48; G01N 30/54; G01N 30/7206; G01N 30/89; G01N 2030/025; G01N 2030/486; G01N 2030/521; G01N 33/0011; G01N 2033/0019; F01N 2330/00; F01N 2570/012
USPC .......................................................... 73/23.3
See application file for complete search history.

(56) References Cited

U.S. PATENT DOCUMENTS

2011/0054938 A1* 3/2011 Hood .................... G01N 33/14
                                                                     705/3

* cited by examiner

*Primary Examiner* — Tarun Sinha
(74) *Attorney, Agent, or Firm* — Chun-Ming Shih; HDLS IPR Services

(57) ABSTRACT

A method for detecting a gas sample includes the following steps of: providing a carbon aerogel sleeve; introducing a gas sample to the carbon aerogel sleeve, and then sequentially extracting, concentrating, activating, and re-concentrating the gas sample adsorbed by the carbon aerogel and detecting a concentration of the re-concentrated gas sample by a gas chromatograph-mass spectrometer (GC-MS); and extracting the carbon aerogel for several hours with reflux in a dichloromethane solvent and a n-hexane solvent several times per hour to remove the residual gas sample, and then drying the extracted carbon aerogel for reuse, wherein the dichloromethane solvent and the n-hexane solvent are at a volume ratio of 0.001-1000.

11 Claims, 6 Drawing Sheets

METHOD FOR DETECTING A GAS SAMPLE USING A CARBON AEROGEL ADSORBENT

FIELD OF THE INVENTION

The present invention is directed to a method for detecting a gas sample, and more particularly to a method for detecting a gas sample using a carbon aerogel adsorbent.

BACKGROUND OF THE INVENTION

Exhaust gas emitted to the environment mainly comes from a stationary source or a mobile source and contains a harmful substance, such as carbon monoxide (CO), nitrogen oxide ($NO_x$), metal, particulate matter (PM), volatile organic compounds (VOCs), or polycyclic aromatic hydrocarbons (PAHs). The conventional adsorbent for PAHs is made of a polymer resin (e.g. Amberlite XAD-2 resin or Amberlite XAD-16 resin) or a polyurethane foam (PUF) material, but this product is very expensive and not easily recovered for reuse.

Therefore, there is a need to replace the XAD-based adsorbent or the PUF-based adsorbent, and the substitute product can lower the manufacture cost and the use cost.

SUMMARY OF THE INVENTION

For replacing the expensive XAD adsorbent to lower the manufacture cost and provide an effective gas-detection model, the inventors disclose a synthesized carbon aerogel adsorbent for detecting a gas sample, which can effectively filter particulate matter, effectively collect PAHs by filtration, lower the cost for materials, and make itself more competitive in practical applications.

For implementing the adsorption test, PAH compounds having toxic equivalency factors (TEFs), such as acenaphthene (ACP), acenaphthylene (ACPy), benzo[a]pyrene (BaP), or dibenz[a,h]anthracene (DBA) are used. In the test, the constant concentration of a test gas is introduced to a detection column filled with a carbon aerogel or an XAD resin under a room temperature and a relative humidity of 80±10% at a low volumetric flow rate for 5, 10, 15, 30, or 60 minutes, and then the PAH concentrations for various gas-introducing duration are measured. For the four PAH compounds, the carbon aerogel has higher adsorption efficiency than the XAD resin. Especially, the XAD resin has poor adsorption efficiency for the linear five benzene ring compound, DBA, and the DBA concentrations can't be measured for any time by using the same material. Additionally, BaP is deemed highly carcinogenic and adsorbed by the XAD resin, which is announced by the Environmental Protection Administration of Taiwan. However, the carbon aerogel has higher adsorption efficiency for BaP than the XAD resin.

During the carbon aerogel manufacture, graphene/graphite oxide is evenly distributed in deionized water, and then the solution is lyophilized after being filled in a glass sleeve. In such a manner, the carbon aerogel can overcome the assembly difficulties to the sleeve with a small diameter. That is, the carbon aerogel has excellent filling properties to containers having various shapes or various sizes.

In the analyzing method for exhaust gas using a chassis dynamometer, a test vehicle is positioned on the chassis dynamometer, and then its engine warms up for a constant duration by a stand-by mode. After which, an exhaust vent of the vehicle is directly connected to a quartz tube. In order to simulate the real driving emission of the vehicle, a dilution chamber and a condensation machine are not considered, and an adsorbing sleeve is connected to the quartz tube. A low-discharged pump is used to ensure the adsorbing sleeve fully collecting a constant volume of the exhaust gas for various driving rates and various driving durations. The collection is performed at an idle speed, a low speed, or a high speed to analyze the adsorption efficiency, the recycling efficiency, and the reuse efficiency of the adsorbent materials.

Further, under the condition of the same driving rate, the adsorption efficiency for total PAHs of the carbon aerogel and the XAD resin increases as the driving duration increases; under the condition of the same driving duration, the adsorption efficiency for total PAHs under the idle speed of the carbon aerogel is the highest. In addition, the engine temperature is so high under the high speed that the fuel combustion is almost complete and the PAH emission amount is low. Therefore, the adsorption efficiency for total PAHs decreases as the driving rate increases.

Further, under the condition of the idle speed, the adsorption efficiency for total PAHs of the carbon aerogel is the highest, which is at least ten times greater than that of the XAD resin.

Further, after the gas collecting under the high speed, the carbon aerogel and the XAD resin are recycled for reuse and the gas collecting is performed again to analyze the reuse efficiency thereof. However, the XAD resin disintegrates after being recycled and reused for multiple times. Accordingly, its adsorption efficiency for total PAHs decreases with the recycling/reusing times increasing. Under the same condition, the carbon aerogel still has the excellent adsorption efficiency for total PAHs.

Therefore, a method for detecting a gas sample is provided, which includes the following steps of: providing a carbon aerogel sleeve produced through a method comprising: acidifying a stacked graphite material with a strong acid, and then adding polyethylene glycol thereto to perform a reaction in a high temperature to obtain a carbon aerogel solution; filling a polyurethane foam material and a glass wool to a bottom of a glass sleeve, and then filling the carbon aerogel solution to the glass sleeve to a proper height; and quickly freezing the carbon aerogel solution, and then drying the frozen solution for several days to remove a solvent thereof to form a carbon aerogel; introducing a gas sample to the carbon aerogel sleeve, and then sequentially extracting, concentrating, activating, and re-concentrating the gas sample adsorbed by the carbon aerogel and detecting a concentration of the re-concentrated gas sample by a gas chromatograph-mass spectrometer (GC-MS); and extracting the carbon aerogel for several hours with reflux in a dichloromethane solvent and a n-hexane solvent several times per hour to remove the residual gas sample, and then drying the extracted carbon aerogel for reuse, wherein the dichloromethane solvent and the n-hexane solvent are at a volume ratio of 0.001-1000.

The present invention exhibits the following advantages:

1. A novel gas-adsorbent material is provided to replace the conventional product made of an expensive XAD resin so as to lower the manufacture cost. A novel method for manufacturing a carbon aerogel is provided, and the carbon aerogel can be connected to an exhaust vent to effectively filter particulate matter and collect PAHs by filtration.

2. The carbon aerogel can achieve the gas-adsorbing efficiency confirming to the current environmental test standards in a small amount. Further, the carbon aerogel can be formed through being filled in glass sleeves of various diameters and then lyophilized so that the assembly difficulties to the sleeve can be overcome.

3. The manufactured carbon aerogel has excellent filling properties to containers having various shapes or various sizes.

4. The carbon aerogel has excellent adsorption efficiency for ACP, ACPy, BaP, and DBA, but the XAD resin can't adsorb the linear five benzene ring type compound, DBA. For BaP, a high carcinogen announced by the Environmental Protection Administration of Taiwan, the carbon aerogel has higher adsorption efficiency than the XAD resin.

5. When a vehicle is operated at an idle speed, the carbon aerogel has the adsorption efficiency for PAHs better than the XAD resin. Therefore, the carbon aerogel can replace the expensive XAD resin to reduce the manufacture cost.

6. The carbon aerogel and the XAD resin are both reusable after being recycled. However, after repeating the recycling and reusing for multiple times, the XAD resin disintegrates and its adsorption efficiency lowers; the carbon aerogel still has an intact structure and maintain its adsorption efficiency as the original level.

DETAILED DESCRIPTION OF THE INVENTION

The detailed description and preferred embodiments of the invention will be set forth in the following content, and provided for people skilled in the art so as to understand the characteristics of the invention.

Figure 1:
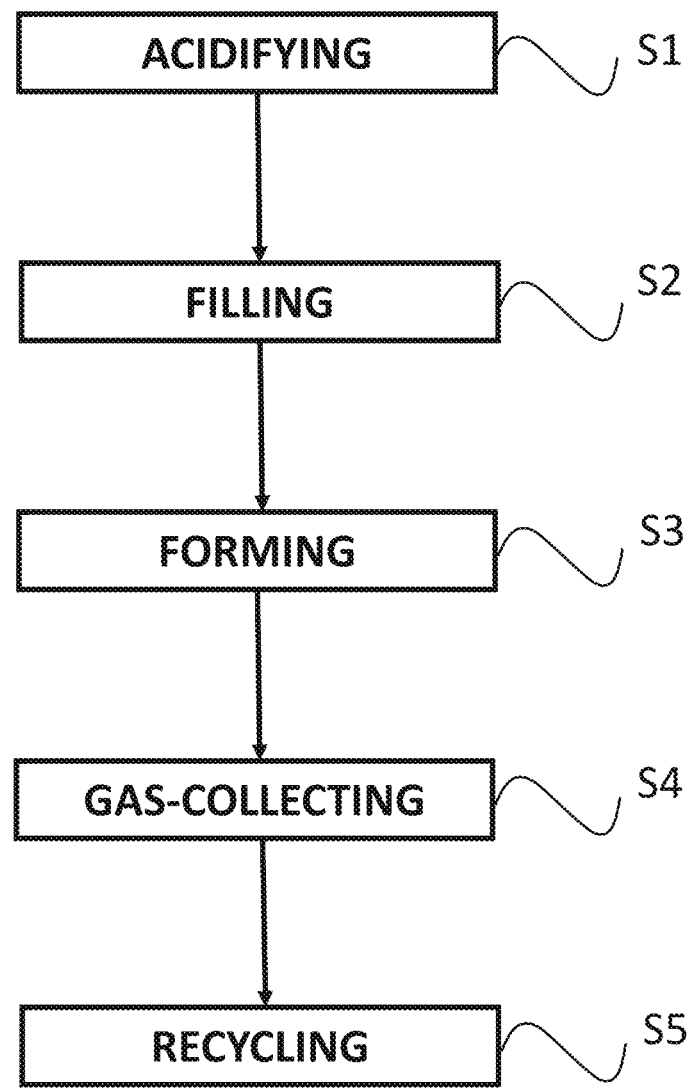
FIG. 1 is a flow chart illustrating the method of the present invention.

As shown FIG. 1, an embodiment of the present invention discloses a method for producing a carbon sleeve and then detecting a gas sample using the sleeve. The disclosed method totally comprises the steps of: an acidifying step (S1), a filling step (S2), a forming step (S3), a gas-collecting step (S4), and a recycling step (S5).

Since the later formed carbon aerogel solution has a multiple-layered graphite having functional groups, a stacked graphite material is acidified with a strong acid in the step (S1). After which, polyethylene glycol is added to the acidic solution to perform a reaction in a high temperature so as to obtain the carbon aerogel solution. Based on the total volume of the carbon aerogel solution, the multiple-layered graphite has a concentration of 0.01-10 g/mL. Since carbon atoms in the carbon aerogel have delocalized electrons to form a ketone group (—C=O), a hydroxyl group (—OH), a carboxyl group (—COOH), an amino group (—NH$_2$), or an imino group (=NH), these carbon atoms can convert the planar structure of the graphite material to a three-dimension structure or a non-planar structure so that the distance between the adjacent two layers increases. In such a manner, the stacked graphite material is delaminated to a single-layered graphene or a multiple-layered graphene. In addition, the carbon aerogel solution further has a solvent, e.g. water, deionized water, or alcohol, for adjusting the graphene concentration.

In the step (S2), a polyurethane foam material and a glass wool are filled to a bottom of a glass sleeve, and then the carbon aerogel solution is filled to the glass sleeve to a proper height.

Figure 2:
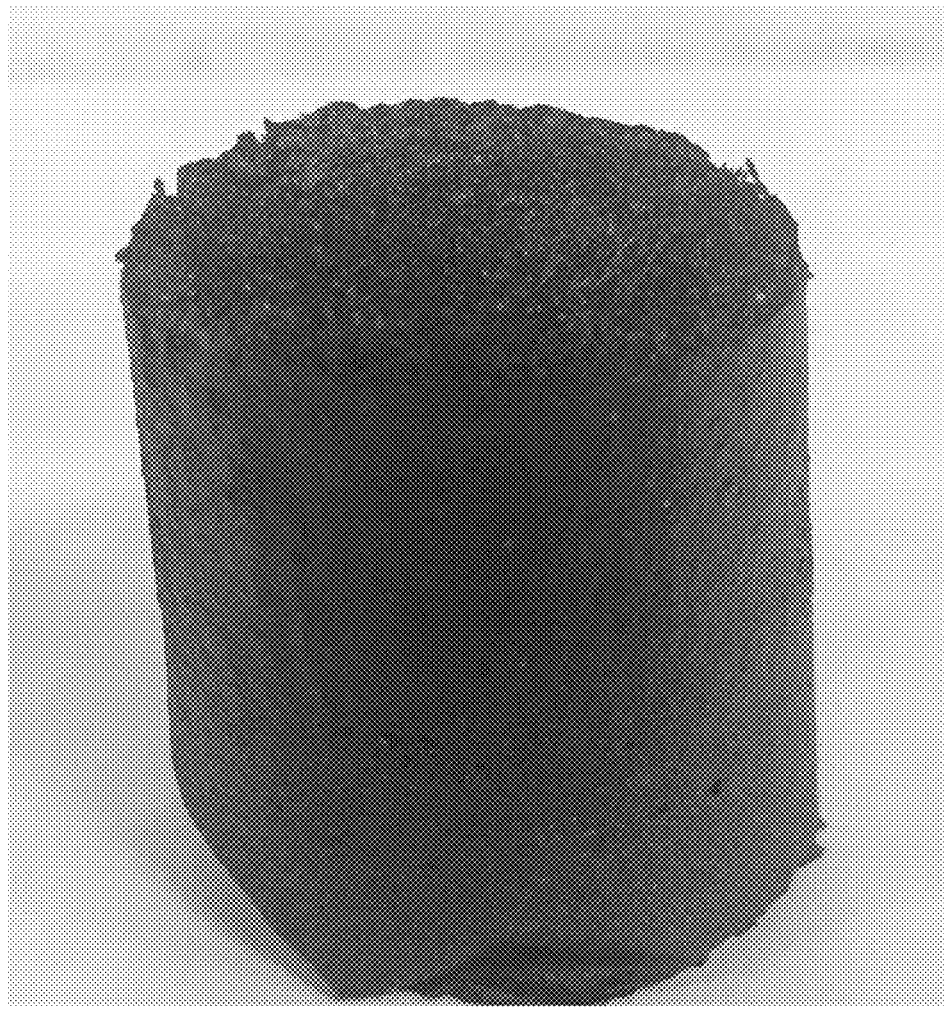
FIG. 2 is a picture showing the carbon aerogel of the present invention.
Figure 3:
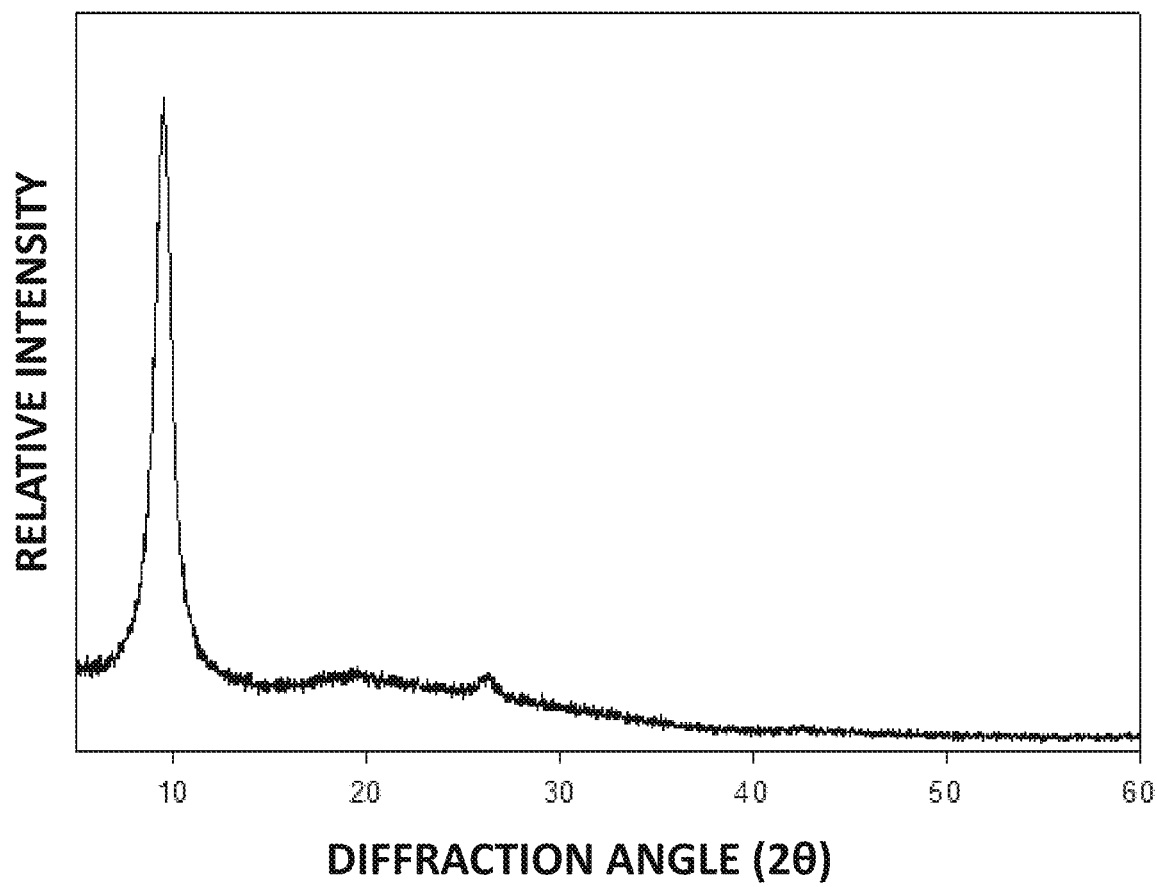
FIG. 3 is an X-ray diffraction (XRD) picture showing the carbon aerogel.
Figure 4A:
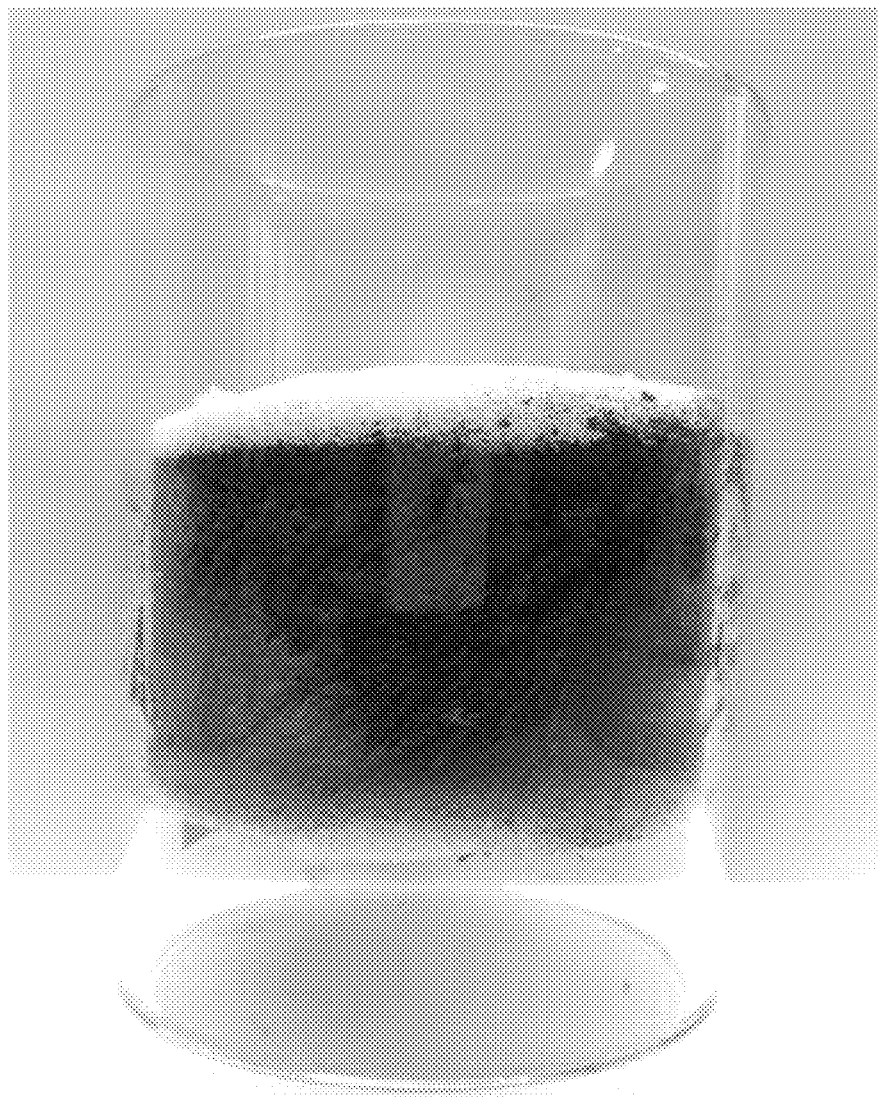
FIG. 4A is a picture showing the carbon aerogel sleeve of the present invention.
Figure 4B:
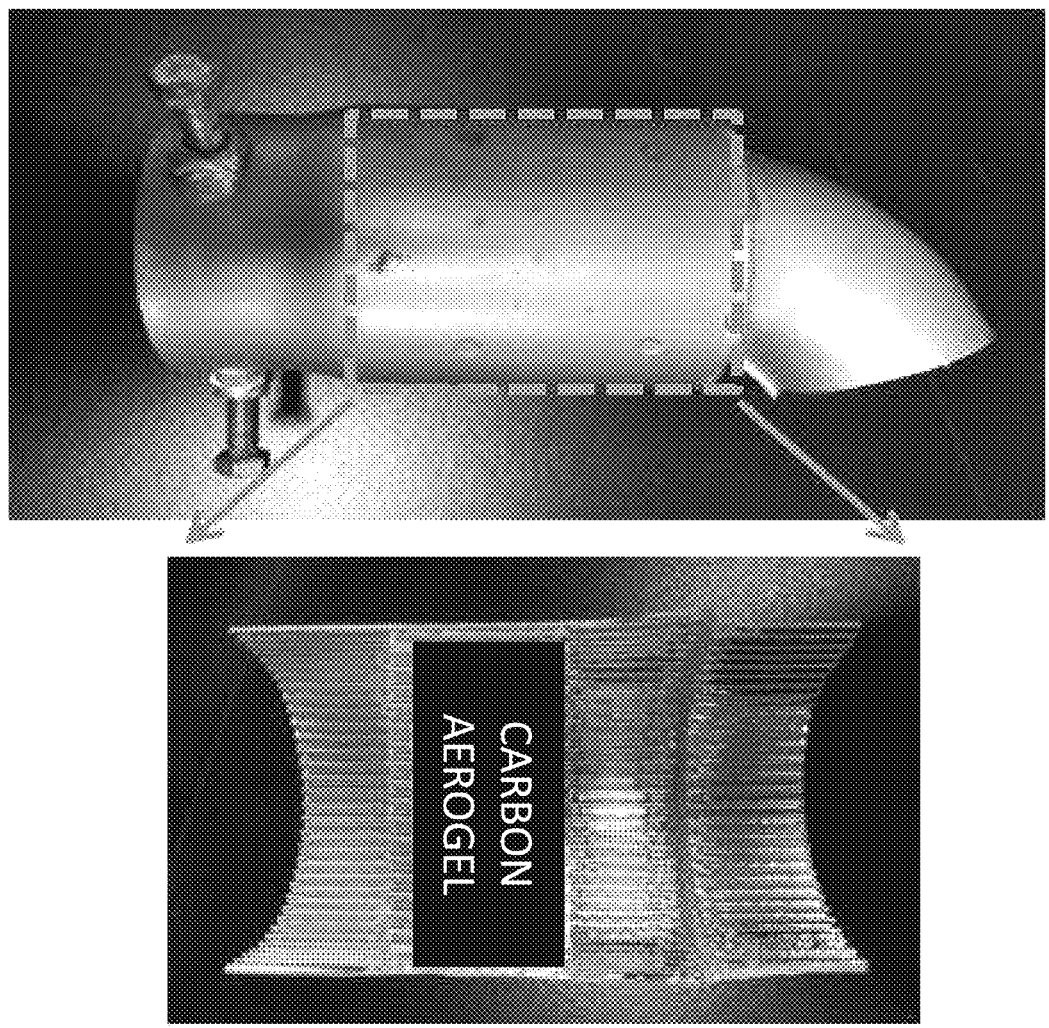
FIG. 4B is a schematic picture showing a flame arrester containing the carbon aerogel of the present invention.

In the step (S3), the carbon aerogel solution is quickly frozen, and then the frozen solution is lyophilized for several days to remove the solvent thereof and dry the frozen solution so as to form a carbon aerogel. Before the following test, the carbon aerogel may be packed in aluminum foil and then stored in −20□. Further, the carbon aerogel has a density of 0.001-100 g/cm$^3$. Additionally, the lyophilization can be replaced with another drying process, e.g. supercritical drying or solvent-extraction drying. The size of the carbon aerogel or the amount or intensity of its functional groups can be adjusted according to the manufacture parameters, e.g. the appearance of the stacked graphite material, the type of graphene, the concentration of strong acid, the type of strong acid, the acid-reaction duration, the polyethylene glycol concentration, or the polyethylene glycol-reaction duration. Further, while the acid-reaction is stronger, the hydrophilic property of the carbon aerogel is more obvious; while the polyethylene glycol-reaction is stronger, the hydrophobic property of the carbon aerogel is more obvious. As such, the hydrophilic/hydrophobic property can correspond to a hydrophilic gas sample or a hydrophobic gas sample in the later test. As shown in FIG. 2, the carbon aerogel looks black and is a carbon block without any support. Accordingly, the carbon aerogel can be formed in any volume or any shape. Since the stacked graphite material has a lot of folds, the carbon aerogel has the elastic deformation property and the recoverability property and has a low Poisson's ratio. As shown in FIG. 3, a graphite sheet has a characteristic peak at a 2θ angle of 26.1 degrees and a distance of 0.34 nm between its two adjacent (002) surfaces. The carbon aerogel has two characteristic peaks each at a 2θ angle of 9.4 degrees and at a 2θ angle of 26.2 degrees and a distance of 0.94 nm between its two adjacent layers. This result implies that the stacked graphite material is delaminated to the single-layered graphene or the multiple-layered graphene, and the carbon aerogel comprises a graphene with a small number of layers. Further as shown in FIG. 4A, the carbon aerogel has excellent filling properties for containers of various shapes or various volumes. As shown in FIG. 4B, the carbon aerogel is filled in a flame arrester, wherein the carbon aerogel is deposited between an upper metal mesh and a lower metal mesh. As such, the flame arrester can collect carbon particles or particulate matter by filtration and further collect the gaseous PAHs in the granule.

Figure 5:
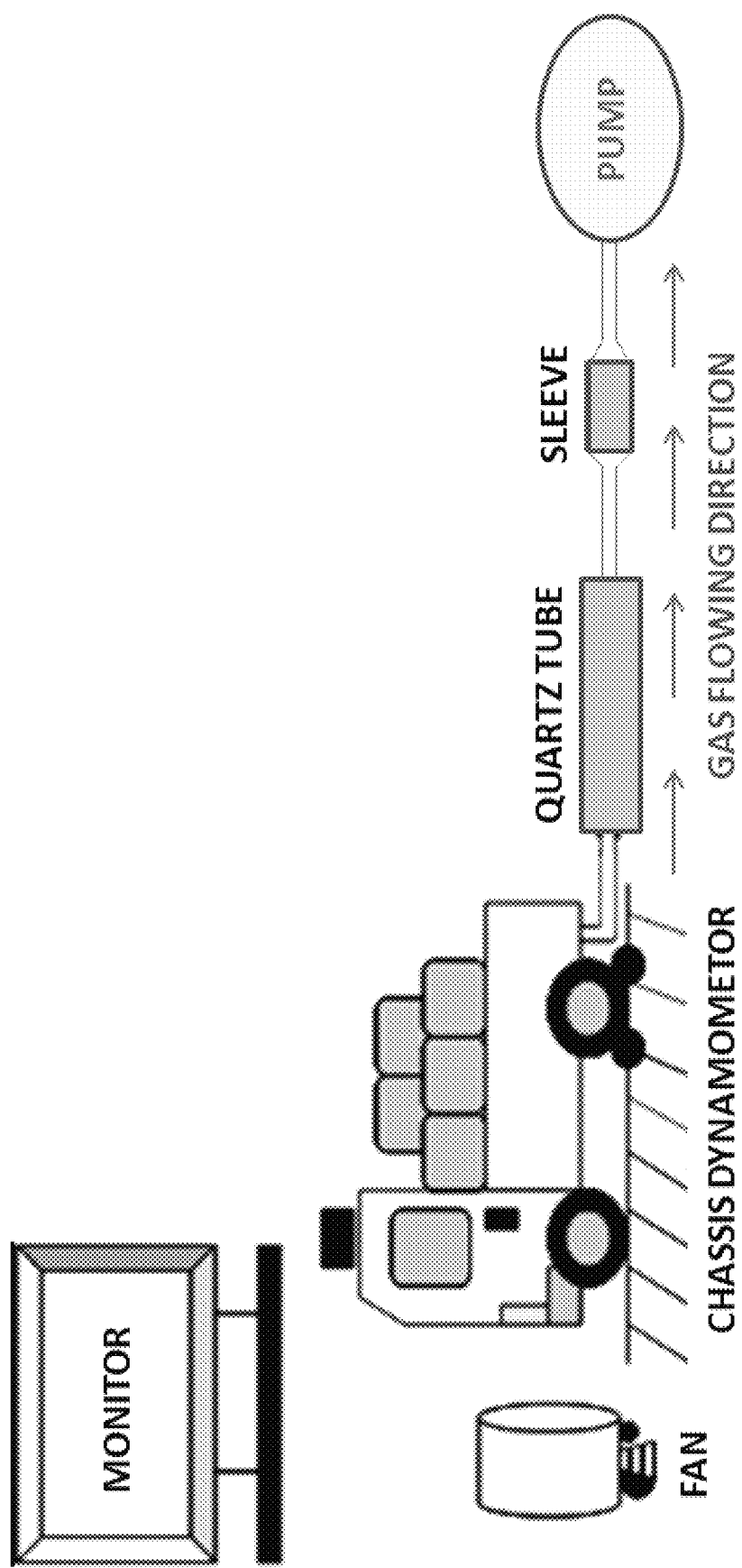
FIG. 5 is a schematic picture showing an exhaust-gas analyzing system using a chassis dynamometer of the present invention.

In the step (S4), a gas sample is introduced to the carbon aerogel sleeve to make the gas sample in contact with the carbon aerogel, and then the gas sample adsorbed by the carbon aerogel is sequentially extracted, concentrated, activated, and re-concentrated according to the procedure published by the Environmental Protection Administration of Taiwan. Afterward, the concentration of the gas sample adsorbed by the carbon aerogel is measured by a gas chromatograph-mass spectrometer. As shown in FIG. 5, the gas sample may be introduced according to an exhaust-gas analyzing system using a chassis dynamometer. Under the same driving rate, the adsorption efficiency for total PAHs of the carbon aerogel and the XAD resin increases as the driving duration increases. Since the engine temperature is high under the high speed and the fuel combustion is almost complete to generate a large number of carbon dioxide and water and emit a small number of PAHs, the adsorption efficiency for total PAHs is the lowest under the high speed for the same adsorbent material. Under the idle speed, the adsorption efficiency for total PAHs of the carbon aerogel is the highest, which is at least ten times greater than that of the XAD resin. Additionally, the gas sample is not limited to the foregoing mobile source gas sample, and may be a stationary source gas sample (emitted from a boiler) or an ambient atmosphere gas sample. Also, the gas sample may contain carbon clusters, carbon particles, particulate matter, gaseous PAHs, solid PAHs, or volatile compounds.

In the step (S5), the carbon aerogel is extracted for several hours with reflux in a dichloromethane solvent and a n-hexane solvent (at a volume ratio of 0.001-1000) several times per hour to remove the residual gas sample. After which, the extracted carbon aerogel is dried for reuse in the next adsorption test. Further, the extracting solvent may contain another polar solvent or another non-polar solvent; an example of the polar solvent is halogen alkane (e.g. methyl chloride), halogen ether, halogen ether, or halogen aromatic hydrocarbon (e.g. chlorobenzene or bromobenzene); an example of the non-polar solvent is alkane (e.g. isohexane), ether, ether, or aromatic hydrocarbon (e.g. benzene or toluene). After the gas collecting with the carbon aerogel and the XAD resin under the high speed, the two adsorbent materials are recycled for reuse and the gas collecting is performed again to analyze the reuse efficiency thereof. However, the XAD resin disintegrates after the XAD resin is recycled and reused for multiple times. Accordingly, its adsorption efficiency for total PAHs decreases with the recycling times increasing. Under the same condition, the carbon aerogel still has the adsorption efficiency for total PAHs as original.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for detecting a gas sample comprising:
    providing a carbon aerogel sleeve produced through a method comprising:
        acidifying a stacked graphite material with a strong acid, and then adding polyethylene glycol thereto to perform a reaction in a high temperature to obtain a carbon aerogel solution;
        filling a polyurethane foam material and a glass wool to a bottom of a glass sleeve, and then filling the carbon aerogel solution to the glass sleeve to a proper height; and
        quickly freezing the carbon aerogel solution, and then drying the frozen solution for several days to remove a solvent thereof to form a carbon aerogel;
    introducing a gas sample to the carbon aerogel sleeve, and then sequentially extracting, concentrating, activating, and re-concentrating the gas sample adsorbed by the carbon aerogel and detecting a concentration of the re-concentrated gas sample by a gas chromatograph-mass spectrometer; and
    extracting the carbon aerogel for several hours with reflux in a dichloromethane solvent and a n-hexane solvent several times per hour to remove the residual gas sample, and then drying the extracted carbon aerogel for reuse, wherein the dichloromethane solvent and the n-hexane solvent are at a volume ratio of 0.001-1000.

2. The detecting method as claimed in claim 1, wherein the solvent of the carbon aerogel solution is water, deionized water, or alcohol.

3. The detecting method as claimed in claim 1, wherein based on total volume of the carbon aerogel solution, the stacked graphite material has a concentration of 0.01-10 g/mL.

4. The detecting method as claimed in claim 1, wherein in the carbon aerogel extracting step, the carbon aerogel is refluxed in a mixture containing the dichloromethane solvent, the n-hexane solvent, and a polar solvent or a non-polar solvent.

5. The detecting method as claimed in claim 4, wherein the polar solvent is halogen alkane, halogen ether, halogen ether, or halogen aromatic hydrocarbon.

6. The detecting method as claimed in claim 4, wherein the non-polar solvent is alkane, ether, ether, or aromatic hydrocarbon.

7. The detecting method as claimed in claim 1, wherein the solution drying step is performed with lyophilization, supercritical drying, or solvent-extraction drying.

8. The detecting method as claimed in claim 1, wherein the carbon aerogel has a density of 0.001-100 g/cm$^3$.

9. The detecting method as claimed in claim 1, wherein the gas sample is a mobile source gas sample, a stationary source gas sample, or an ambient atmosphere gas sample.

10. The detecting method as claimed in claim 1, wherein the gas sample contains carbon clusters, carbon particles, particulate matter, gaseous polycyclic aromatic hydrocarbons, solid polycyclic aromatic hydrocarbons, or volatile compounds.

11. The detecting method as claimed in claim 1, wherein the gas sample contains acenaphthene, acenaphthylene, benzo[a]pyrene, or dibenz[a,h]anthracene.

* * * * *